US00RE35687E

United States Patent [19]

Igaue et al.

[11] E Patent Number: Re. 35,687

[45] Reissued Date of Patent: *Dec. 9, 1997

[54] DISPOSABLE GARMENTS OF PANTS TYPE

[75] Inventors: Takamitsu Igaue, Kawanoe; Hironori Nomura, Iyomishima; Taiji Shimakawa, Kanonji; Tohru Sasaki, Kawanoe, all of Japan

[73] Assignee: Uni-Charm Corporation, Ehime-ken, Japan

[ * ] Notice: The term of this patent shall not extend beyond the expiration date of Pat. No. 5,055,103.

[21] Appl. No.: 393,620

[22] Filed: Feb. 23, 1995

Related U.S. Patent Documents

Reissue of:

[64] Patent No.: 5,188,627
Issued: Feb. 23, 1993
Appl. No.: 665,426
Filed: Mar. 5, 1991

[30] Foreign Application Priority Data

Mar. 12, 1990 [JP] Japan ..... 2-60768
Sep. 27, 1990 [JP] Japan ..... 2-259834

[51] Int. Cl.[6] ..... A61F 13/15

[52] U.S. Cl. ..... 604/385.2; 604/358; 604/393; 604/396

[58] Field of Search ..... 604/358, 378, 604/384, 385.1, 385.2, 393, 396

[56] References Cited

U.S. PATENT DOCUMENTS

| | | |
|---|---|---|
| Re. 31,922 | 6/1985 | Mesek et al. . |
| 4,695,278 | 9/1987 | Lawson . |
| 4,704,116 | 11/1987 | Enloe . |
| 4,738,677 | 4/1988 | Foreman . |
| 4,822,435 | 4/1989 | Igaue et al. . |
| 4,900,317 | 2/1990 | Buell . |
| 4,904,251 | 2/1990 | Igaue et al. . |
| 5,055,103 | 10/1991 | Nomura et al. . |
| 5,092,861 | 3/1992 | Nomura et al. . |

FOREIGN PATENT DOCUMENTS 2212382 7/1989 United Kingdom .

*Primary Examiner*—Robert A. Clarke
*Attorney, Agent, or Firm*—Lowe, Price, LeBlanc & Becker

[57] ABSTRACT

Disposable garments of pants type having a waist-opening with a first elastic member, a pair of leg-openings with second elastic members and a pair of cuff members with third elastic members which are inwardly spaced from said second elastic members, respectively and thereby said leg-openings are provided with double elastically stretchable seal structures.

5 Claims, 4 Drawing Sheets

DISPOSABLE GARMENTS OF PANTS TYPE

Matter enclosed in heavy brackets [ ] appears in the original patent but forms no part of this reissue specification; matter printed in italics indicates the additions made by reissue.

BACKGROUND OF THE INVENTION

The present invention relates to disposable garments of pants type and more particularly to such garments such as baby training pants having respective leg-openings provided with double elastically stretchable seal structures, respectively.

The disposable baby training pants are well known, in which the waist-opening and the pair of leg-openings are provided with the elastic members. However, young children wearing such training pants are generally active in their walking and movements, so excretion leak often occurs around the leg-openings.

Accordingly, it is an object of the invention to provide disposable garments of pants type further including cuff members containing therein elastic members inwardly spaced from the outer edges of the respective leg-openings so that the above-mentioned problem is eliminated.

SUMMARY OF THE INVENTION

The object set forth above is achieved, in accordance with the present invention, by disposable garments of pants type having a waist-opening provided with a first elastic member and a pair of leg-openings provided with ring-like second elastic members, wherein there are provided a pair of cuff members inwardly spaced from the respective second elastic members and said cuff members are adapted to rise against the user's skin under a contractile force of third elastic members contained therein.

In a preferable embodiment, with the garments unfolded and respective opposed side edges of front and rear bodies thereof being still not bonded together, said second elastic members for the respective leg-openings are positioned to be curved inward while said third elastic members for the cuff members are positioned substantially in parallel to the longitudinal axis of the garments so that, once put on the user's body, elastically stretchable lines defined by said second elastic members partially intersect elastically stretchable lines defined by said third elastic members so as to bias said cuff members against the user's skin.

Preferably, an inner sheet forming an inner surface of the garments comprises an elastically stretchable, water-permeable sheet, an outer sheet forming an outer surface of the garments comprises an ealstically stretchable, water-impermeable sheet and said cuff members comprise a moisture-permeable sheets.

With the garments of the invention constructed as has been described above, the cuff members inwardly spaced from the respective second elastic members are adapted to rise against the user's skin under the contractile force of the third elastic members contained therein and thus the respective leg-openings are provided with the inner and outer seals. In this manner, excretion leak possible occurring around said leg-openings is effectively prevented thereby, even if walk and movements of the user is active.

Once put on the user's body, the elastically stretchable lines defined by said second elastic members partially intersect the elastically stretchable lines defined by said third elastic members so as to bias said cuff members against the user's skin. This feature is effective to prevent said cuff members from being laid down outward so that said cuff members can effectively serve as barriers against excretion. In other words, said cuff members hold excretion inside them. Accordingly, prevention of excretion leak around the leg-openings is further enhanced.

Said inner and outer sheets forming the inner and outer surfaces of the garments, respectively, comprise the elastically stretchable material, so said inner and outer sheets are adapted for expansion and contraction to accommodate movement of the user. Such feature provides comfortableness and fitness when the user has it on.

BRIEF DESCRIPTION OF THE DRAWINGS

An embodiment of the garments constructed according to the invention is illustrated by the accompanying drawings, in which.

PREFERRED EMBODIMENT OF THE INVENTION

The present invention will be described by way of embodiments in reference with the accompanying drawings.

Figure 1:
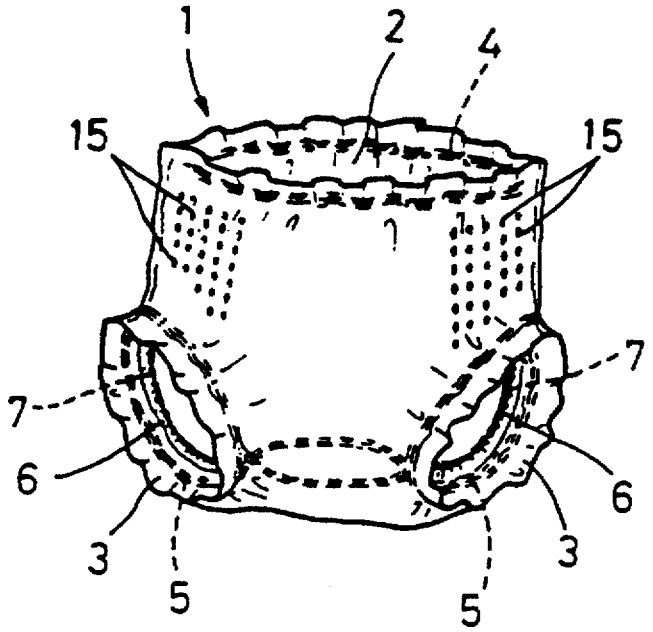
FIG. 1 is a perspective view of this embodiment.
Figure 2:
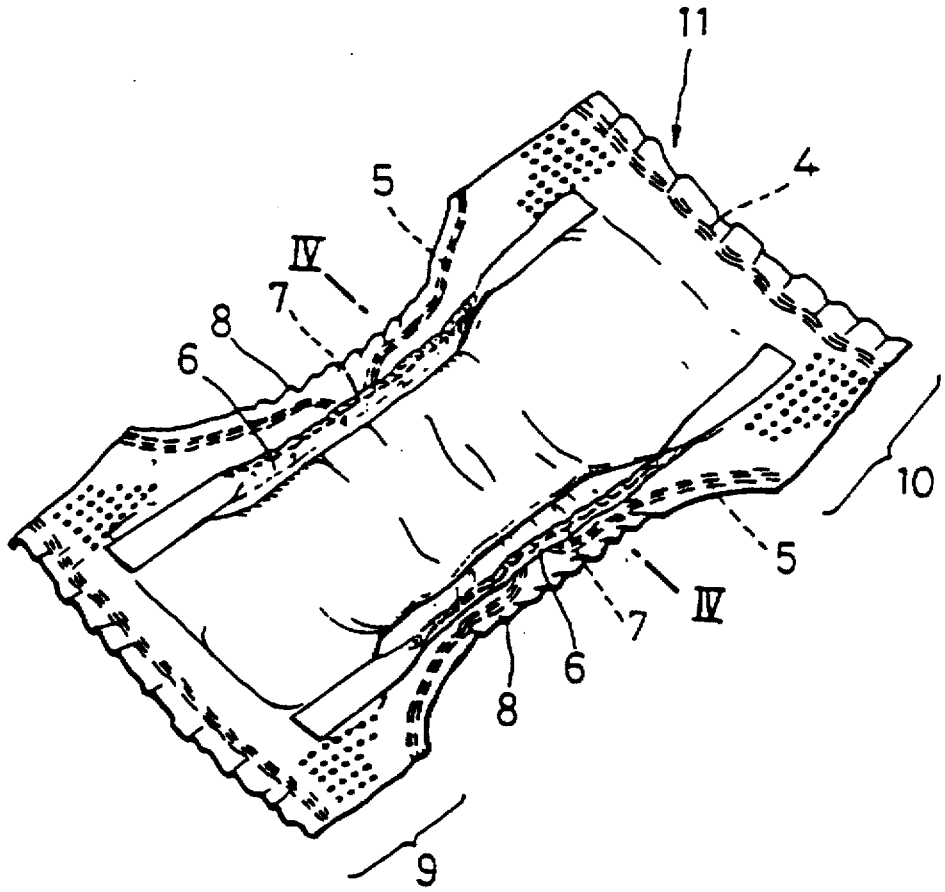
FIG. 2 is a developed perspective view showing the same with front and rear bodies being separated from each other.

As shown by FIGS. 1 and 2, the garments 1 have a waist-opening 2 and a pair of leg-openings 3, these openings being provided along regions adjacent their edges with associated elastic members 4, 5 fixed therein. The garments 1 further comprise cuff members 6 extending along the respective leg-openings 3 inwardly spaced from the respective elastic members 5 and each of the cuff members 6 wraps therein an elastic member 7. Referring to FIG. 2 showing a laminate 11 as being unfolded, front and rear bodies 9, 10 of this laminate 11 may be bonded together along thier opposite side edges except respective leg-openings defining portions 8 to form the garments of pants type.

Figure 3:
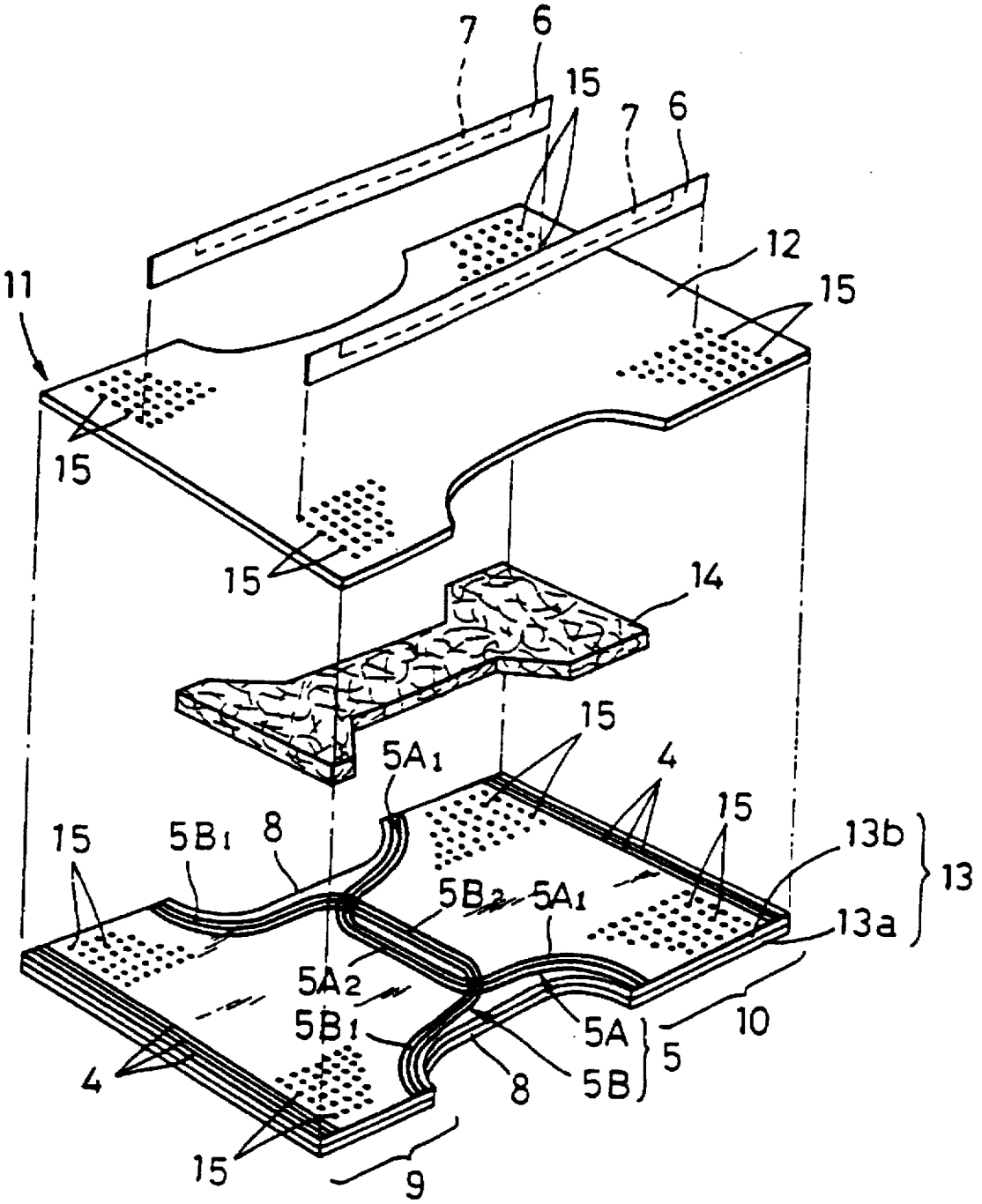
FIG. 3 is an exploded perspective view of the same.
Figure 4:
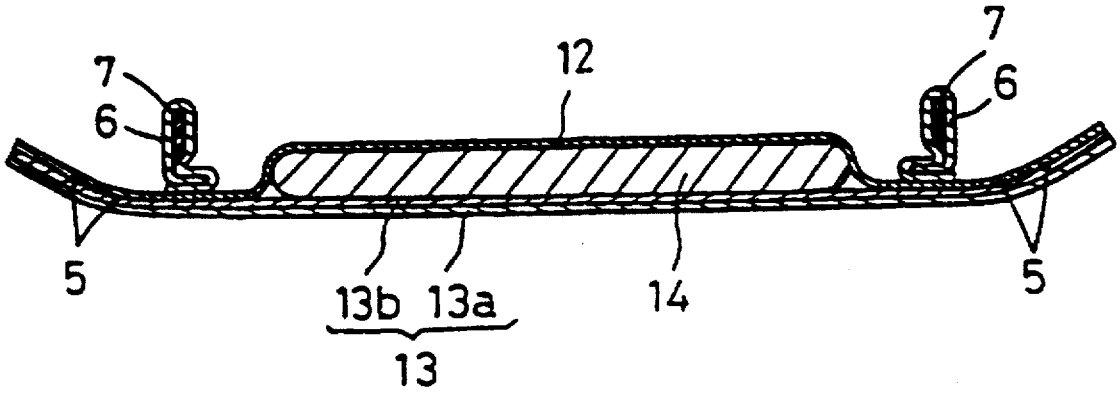
FIG. 4 is a sectional view taken along a line IV—IV in FIG. 2.

Referring to FIGS. 3 and 4, the laminate 11 comprises an inner sheet 12 made of elastic, water-permeable non-woven fabric to form an inner surface of the garments, an outer sheet 13 made of elastic, water-impermeable elastomer sheet 13b such as plastic or rubber sheet laid on the inner surface of non-woven fabric 13a which is substantially similar to said non-woven fabric sheet 12 to form an outer surface of the garments 1, and a mat- or sheet-like sandglass-shaped absorbent core 14 molded from a mixture of fluff pulp, thermoplastic fibres and water-insoluble, super water-absorptive polymer powder.

Said elastic, water-permeable non-woven fabric may be obtained preferably by carding heat crimped fibres having a basic weight of 25 to 45 g/m$^2$ and a fineness of 0.5 to 3 d to form web and then heat treating this web so as to present a sheet-like form.

The elastomer sheet 13b preferably has an elastic strength (stretch stress) higher than those of the non-woven fabric 12, 13a. However, these components may have substantially same elastic strength.

A crotch zone defined between the front and rear bodies 9, 10 each including the inner and outer sheets 12, 13 is formed along opposite side edges with inwardly curved notches corresponding to the previously mentioned respective leg-opening defining portions 8. The waist-opening defining portions extending along longitudinal ends of the front and rear bodies 9, 10 and the respective leg-opening defining portions 8 are provided adjacent the edges thereof with the respective elastic members 4, 5 so as to be sandwiched between the inner sheet 12 and the elastomer sheet 13b. The elastic members 4 for the waist-opening are bonded with hot melt adhesive and under a stretched condition to the outer sheet 12 and/or the elastomer sheet 13b in parallel to the longitudinal ends of the front and rear bodies 9, 10. The elastic members 5 for the leg-openings comprise a first members 5A and a second members 5B. The first and second members 5A, 5B intersect each other at points therealong adjacent opposite ends of the respective members 5A, 5B and sections $5A_1$, $5B_1$ extending outward from the respective intersecting points are bonded also with hot melt adhesive and under a stretched condition to the inner surface (s) of the inner sheet 12 and/or the elastomer sheet 13b along the edges of the respective leg-opening defining portions 8. Intermediate sections $5A_2$, $5B_2$ extending between said intersecting points are bonded neither to these sheets nor to the core 14 and merely positioned on the underside of said core 14 in a central zone thereof.

The core 14 has its top surface fixed to the inner sheet 12 with dots of hot melt adhesive. Thereby, not only any movement of the core 14 can be minimized but also it can be avoided that absorption of liquid excretion through the inner sheet 12 into the core 14 would be more or less obstructed when the inner sheet 12 floats off from the top surface of the core 14. Furthermore, any interference with elastic expansion and contraction of the inner and outer sheets 12, 13 can be also thereby minimized.

The inner sheet 12 is provided on its top surface with the cuff members 6 inwardly spaced from the end sections $5A_1$, $5B_1$ of the elastic members 5, substantially in parallel to the longitudinal axis of the laminate 11. Each of the cuff members 6 comprises a single sheet of moisture-permeable but water-impermeable non-woven fabric folded into a sleeve. One side edge of this sleeve wraps therein the elastic member 7 being bonded therto under a stretched condition with hot melt adhesive and the other side edge is bonded also with hot melt adhesive to the top surface of the inner sheet 12. The cuff member thus constructed is laid down outward and bonded at longitudinally opposite ends to the top surface of the inner sheet 12 with hot melt adhesive. However, it is also possible that the cuff member 6 is laid down inward and bonded at the longitudinally opposite ends to the top surface of the inner sheet 12. No matter which direction the cuff member 6 is laid down, the cuff member 6 rises under a contractile force of the elastic member 7 even after the cuff member 6 has been bonded at the longitudinally opposite ends to the top surface of the inner sheet 12. It is also obviously possible to bond the cuff member 6 onto th top surface of the inner sheet 12 by means of welding process.

In this laminate 11, the inner and outer sheets 12, 13 are provided in zones of the front and rear bodies 9, 10 extending outside the respective cuff members 6 (i.e., zones in which the core 14 is absent) with a plurality of vent holes 15. These vent holes 15 each having a diameter of 0.2 to 2 mm are formed by a group of heating needles or projections arranged at given intervals preferably so that non-woven fabric 12, 13a exposed along the inner periphery of each vent hole are welded together by material of the elastomer sheet 13b which is also exposed along said inner periphery of each vent hole.

The inner sheet 12 and the outer sheet 13 may be bonded together along their outer peripheries, if desired, by means of heat seal, sonic sea/or hot melt adhesive.

The laminate 11 constructed in this manner is folded in two along the longitudinally middle line, then the respectively opposed side edges of the front and rear bodies 9, 10 are heat- or sonic sealed to form the garments 1 as shown in FIG. 1. This seal is adapted to avoid that said respective opposed side edges of the front and rear bodies 9, 10 might be accidentally torn off during its use, but to be easily torn off when the garments are taken off. Preferably, such seal may be inermittently provided along said respectively opposed side edges of the front and rear bodies 9, 10.

Figure 5:
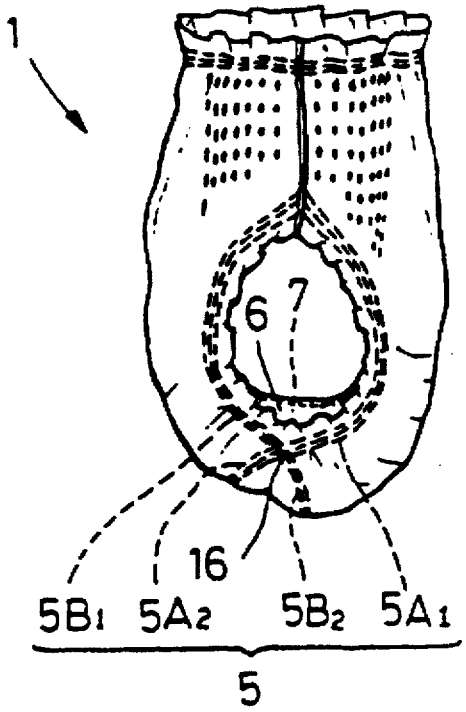
FIG. 5 is a side view of the same.

Referring to FIG. 5 showing the completely assembled garments 1, the elastically stretchable lines defined by the end sections $5A_1$, $5B_1$ of the elastic member 5 extending along the leg-opening 3 intersect the elastically stretchable line defined by the elastic member 7 in the associated cuff member 6 inwardly spaced from said end sections $5A_1$, $5B_1$ and thereby function to bias the opposite ends of the cuff member 6 inward while the intersecting point 16 of the end sections $5A_1$, $5B_1$ or the intermediate sections $5A_2$, $5B_2$ of the elastic member 5 functions to bias a practically middle portion of the cuff member 6 inward. Once put on the user's body, the garments 1 may be somewhat deformed with respect to the condition as shown by FIG, 5, but the above-mentioned biasing effect is maintained, i.e., the outer portion containing the elastic member 5 inwardly biases the associate cuff member 6.

Obviously, the elastic members 5, 7 independently function. Specifically, the elastic members 5 bias the outer edges of the respective openings 3 against the user's skin and the elastic members 7 bias the respective cuff members 6 against the user's skin. However, the above-mentioned cooperation of the elastically stretchable lines defined by the elastic members 5, 7 respectively, enhances the reliability with which the cuff members 6 are biased against the user's skin. Accordingly, the cuff members 6 effectively block excretion leak and, even if any quantity of excretion leaks outward beyond the cuff members 6, this can be blocked by the portions of the respective leg-openings containing therein the elastic members 5.

Interposition of said elastomer sheet 13b is advantageous in that, even if fibre-entanglement or fibre-bond in non-woven fabric as basic material of the inner and outer sheets 12, 13 are loosened when the laminate is stretched, the elastomer sheet prevents the elastic strength, particularly the contractile stress from rapidly decreasing and maintains a desired contractile stress of the laminate as well as a desired fitness of the garments to the user's body.

Figure 6:
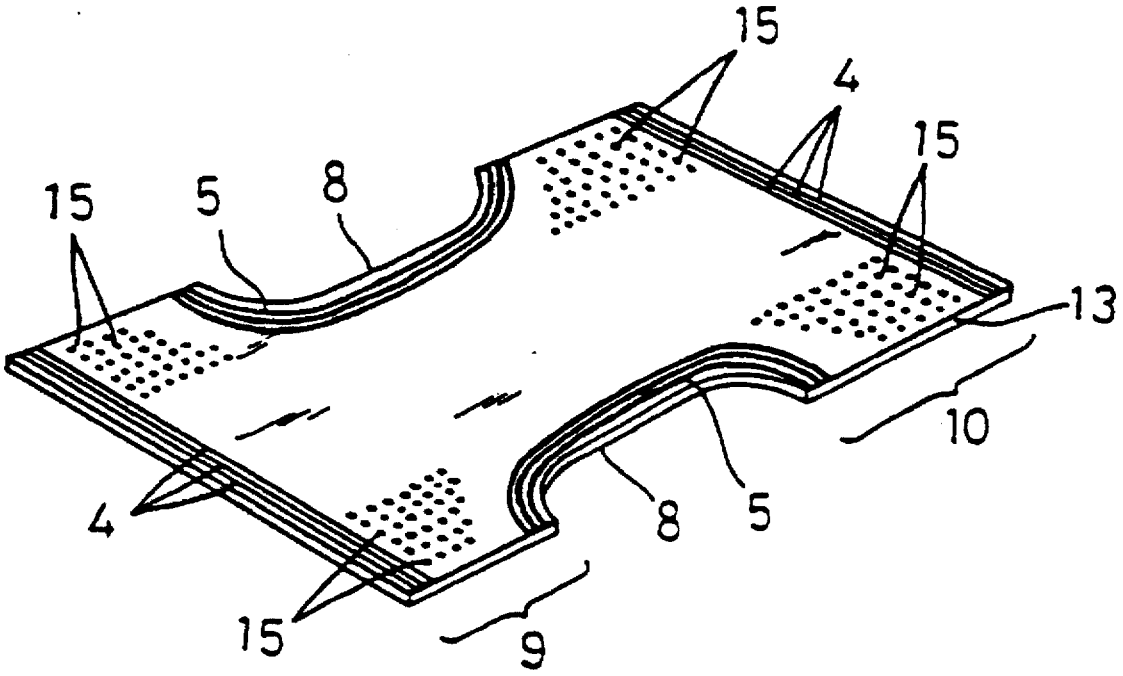
FIG. 6 is a perspective view showing another embodiment of the outer sheet.

FIG. 6 is a perspective view of another embodiment of the outer sheet 13. According to this embodiment, the outer sheet 13 consists of a single layer of elastically stretchable, water-impermeable elastomer sheet such as a plastic or rubber sheet and the elastic members for the respective leg-openings extend only around the respective legs. The remainder is similar to the previously described embodiment. This embodiment advantageously saves material of the outer sheet and the elastic members 5 in comparison with the previous embodiment and thereby can reduce the manufacturing cost of the garments correspondingly.

What is claimed is:

[1. Disposable garments of pants type having a waist-opening provided with a first elastic member and a pair of leg-openings provided with ring-like second elastic members, wherein there are provided a pair of cuff members inwardly spaced from said second elastic members, respectively, and these cuff members are adapted to rise against the user's skin under a contractile force of third elastic members contained in these cuff members, respectively, wherein, with the garments unfolded and respective opposed side edges of front and rear bodies thereof being still not bonded together, said second elastic members for the respective leg-openings are positioned to be curved inward while said third elastic members for the cuff members are positioned substantially in parallel to the longitudinal axis of the garments so that, once put on the user's body, elastically stretchable lines defined by said second elastic members partially intersect elastically stretchable lines defined by said third elastic members so as to bias said cuff members against the user's skin.]

2. Disposable garments of pants type as recited in claim [1,] *6* wherein an inner sheet forming an inner surface of the garments comprise an elastically stretchable, water-permeable sheet, an outer sheet forming an outer surface of the garments comprise an elastically stretchable, water-impermeable sheet and said cuff members comprise a moisture-permeable sheets.

[3. Disposable pants that contain a single waist opening (2) and two leg openings (3) and an absorbent core (14) sandwiched between a water-permeable inner sheet (12) and a water-impermeable outer sheet (13), the improvement which comprises (a) a first elastic member (4) mounted in said waist opening (2) which applies a contractile force to said waist opening (2), (b) ring-like second elastic members (5) provided in each leg opening (3), (c) spaced apart cuff members (6) mounted on said inner sheet (12) at least partially inwardly from said second elastic members (5), said cuff members (6) extending along lines that are substantially parallel to each other and substantially parallel to the longitudinal axis of the pants, and said cuff members (6) are formed from a moisture-permeable but water-impermeable non-woven fabric, and (d) a third elastic member (7) mounted within each cuff member (6) so as to exert a contractile force that causes each cuff member (6) to rise against the leg of a person wearing the pants, a portion of the elastically stretchable lines defined by said second elastic members (5) extend toward the longitudinal axis of the pants and partially intersect the elastically stretchable lines defined by said third elastic members (7) so as to bias said cuff members (6) against the user's skin.]

4. Disposable pants according to claim [3] *7* wherein said outer sheet (13) is elastically stretchable.

5. Disposable pants according to claim [3] *7* wherein the ring-like second elastic members (5) provided around each leg opening (3) are connected to each other by extending across the crotch area of the disposable pants.

*6. Disposable garments of pants type having a waist opening provided with a first elastic member and a pair of leg-openings provided with ring-like second elastic members, wherein there are provided a pair of cuff members inwardly spaced from said second elastic members, respectively, and these cuff members are adapted to rise against the user's skin under a contractile force of third elastic members contained in these cuff members, respectively, wherein, with the garments unfolded and respective opposed side edges of front and rear bodies thereof being still not bonded together, said second elastic members for the respective leg-openings are positioned to be curved inward while said third elastic members for the cuff members are positioned substantially in parallel to the longitudinal axis of the garments so that, once put on the user's body, elastically stretchable lines defined by said second elastic members partially intersect elastically stretchable lines defined by said third elastic members.*

*7. Disposable pants that contain a single waist opening and two leg openings and an absorbent core sandwiched between a water-permeable inner sheet and a water-impermeable outer sheet, the improvement which comprises*

*(a) a first elastic member mounted in said waist opening which applies a contractile force to said waist opening,*

*(b) ring-like second elastic members provided in each leg opening,*

*(c) spaced apart cuff members mounted on said inner sheet at least partially inwardly from said second elastic members, said cuff members extending along lines that are substantially parallel to each other and substantially parallel to the longitudinal axis of the pants, and said cuff members are formed from a moisture-permeable but water impermeable non-woven fabric,*

*(d) a third elastic member mounted within each cuff member so as to exert a contractile force that causes each cuff member to rise against the leg of a person wearing the pants,*

*a portion of the elastically stretchable lines defined by said second elastic members extend toward the longitudinal axis of the pants and partially intersect the elastically stretchable lines defined by said third elastic members.*

* * * * *